United States Patent [19]

Gosselink et al.

[11] 4,165,334
[45] Aug. 21, 1979

[54] DETERGENT COMPOUNDS AND COMPOSITIONS

[75] Inventors: Eugene P. Gosselink, Cincinnati; James M. Richmond, Fairfield; George E. Wentler, West Chester, all of Ohio

[73] Assignee: The Procter & Gamble Company, Cincinnati, Ohio

[21] Appl. No.: 804,490

[22] Filed: Jun. 7, 1977

Related U.S. Application Data

[63] Continuation of Ser. No. 610,595, Sep. 5, 1975, abandoned.

[51] Int. Cl.² .................. C07C 141/02; C07C 141/16
[52] U.S. Cl. ........................... 260/458 R; 260/458 C; 260/513 R; 260/512 R; 562/431; 562/581; 252/551; 252/554; 252/558; 252/171
[58] Field of Search .................. 260/458 R, 458 C

[56] References Cited

U.S. PATENT DOCUMENTS

| | | | |
|---|---|---|---|
| 2,813,898 | 11/1957 | Gaertner | 260/513 R |
| 3,184,477 | 5/1965 | Baird et al. | 260/458 R |
| 3,925,262 | 12/1975 | Laughlin et al. | 260/501.12 |
| 3,929,678 | 12/1975 | Laughlin et al. | 260/501.12 |

OTHER PUBLICATIONS

Kirk-Othmer, Encyclopedia of Chemical Technolgy, vol. 19, pp. 531–532 (1969).

*Primary Examiner*—Nicky Chan
*Attorney, Agent, or Firm*—Jerry J. Yetter; Richard C. Witte; Thomas H. O'Flaherty

[57] ABSTRACT

Compounds of the formula

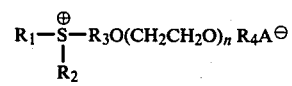

wherein $R_1$ and $R_2$ are each straight chain, branched chain or cyclic alkyl, alkenyl, aryl, aralkyl or alkaryl moieties having from 1–30 carbon atoms; $R_3$ is a $C_2$–$C_8$ alkylene, alkenylene, arylene or alkarylene moiety; $R_4$ is a $C_1$–$C_8$ alkylene, alkenylene, arylene or alkarylene moiety; A is a water-solubilizing anionic moiety; and n is from 1 to about 100 are useful as surfactants. Compounds wherein groups $R_1$, $R_2$ and $R_3$ and integer n are selectively chosen provide good clay soil detergency performance even in the absence of builders. The compounds are usefully combined with other organic surfactants to provide detergent compositions having good clay and oily soil removal performance.

7 Claims, No Drawings

DETERGENT COMPOUNDS AND COMPOSITIONS

This is a continuation of application Ser. No. 610,595, filed Sept. 5, 1975, now abandoned.

BACKGROUND OF THE INVENTION

This invention relates to ethoxylated sulfonium zwitterionic compounds which exhibit unexpectedly high clay soil removal even in very low built or unbuilt detergent systems and which are surprisingly stable under alkaline conditions. The invention further relates to detergent compositions containing the novel sulfonium compounds in combination with co-surfactants and/or builders.

While a variety of surfactant classes are known, e.g., nonionic, anionic, cationic and zwitterionic, none of the conventional types of detersive surfactants are known to provide the advantageous performance of the instant compounds. The shortcomings of the commonly-used surfactants are well-known, and such materials must be built and/or otherwise precisely formulated to provide good soil removal under a variety of conditions.

Efforts have been made to prepare specific types of surfactants for particular purposes and, in particular, zwitterionic compounds have been thoroughly explored and attempts have been made to tailor these compounds in a particular way which would provide especially useful detersive surfactants.

Such known zwitterionic surfactants have generally been based on a nitrogen cation and surfactant classes such as the ammonio-sulfates, ammonio-sulfonates and ammonio-carboxylates have been proposed. The analogous materials based upon a phosphorus cation have also been suggested, although very much less frequently.

While certain of the above mentioned classes of compounds have been found to provide useful detergent properties, they have not, for several reasons, enjoyed any substantial commercial success. One reason for this may be that questions have been raised regarding the environmental effect of materials containing nitrogen or phosphorus.

Also, such surfactants have been expensive to prepare commercially.

It is an object of the present invention to provide zwitterionic detergent compounds which are effective in removing particulate soil from fabrics, and which do not contain nitrogen or phosphorus.

It is another object herein to provide detergent compositions which can be used to cleanse both fabrics and hard surfaces without the need for builders or additives.

DESCRIPTION OF THE PRIOR ART

Various zwitterionic compounds are well known, and it is also known to include oxygen-containing moieties in the charge-separating part of the molecule. In particular, U.S. Pat. No. 3,684,427, issued Aug. 15, 1972 to Walz and Ouaedvlizg relates to certain ethoxylated zwitterionic compounds having long ethoxylate chains, the compounds being useful as dyeing assistants. Also, German Offenlegungschrift No. 2,009,802, published Nov. 5, 1970 and assigned to CIBA Ltd. refers generally to ethoxylated ammonio-sulphates as dyeing assistants. Belgian Pat. No. 813,052, issued to GAF Corporation, concerns amphoteric surfactants having an N,N-bis-(ethoxylate sulfate) structure. U.S. Pat. Nos. 3,452,066, issued June 24, 1969, and 2,781,390, issued Feb. 12, 1957, both to Mannheimer, broadly relate to various zwitterionic surfactants optionally containing a seemingly limitless variety of oxygen-containing, presumably hydrophilic, moieties, including alkylene oxides. U.S. Pat. No. 3,769,311, issued Oct. 30, 1973, to Armstrong and Dawald, discloses ethoxylated ammonio propionate zwitterionics, and describes compounds having limited ranges of ethyleneoxy and hydrophobic groups attached to the positive charge center.

Four co-pending applications, all assigned to the present assignee, relate to particular ethoxylated zwitterionic compounds based on a nitrogen cationic center. These are the applications of R. G. Laughlin, E. P. Gosselink, W. A. Cilley and V. P. Heuring, entitled DETERGENT COMPOUNDS, Ser. No. 493,951, filed Aug. 1, 1974, now abandoned in favor of application Ser. No. 603,837, filed on Aug. 1, 1974; R. G. Laughlin, E. P. Gosselink and W. A. Cilley, entitled DETERGENT COMPOUNDS, Ser. No. 493,956, filed Aug. 1, 1974, now abandoned; R. G. Laughlin and Robert L. Stewart, entitled DETERGENT COMPOSITION HAVING ENHANCED PARTICULATE SOIL REMOVAL PERFORMANCE, Ser. No. 493,952, filed Aug. 1, 1974, now U.S. Pat. No. 3,925,262; and R. G. Laughlin and V. P. Heuring, DETERGENT COMPOSITIONS HAVING ENHANCED PARTICULATE SOIL REMOVAL PERFORMANCE, Ser. No. 493,953, filed Aug. 1, 1974, now U.S. Pat. No. 3,929,678.

In contrast to the numerous patents relating to nitrogen-based zwitterionics, there is relatively little prior art relating to sulfonium zwitterionic compounds. U.S. Pat. No. 2,813,898, assigned to Monsanto, discloses compounds of the general formula

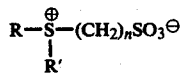

wherein R and R' are hydrocarbon radicals containing from 1 to 18 carbon atoms and n is 1–4. The compounds having a long chain alkyl group are stated to possess surface active properties.

The German Specification No. 943,830, assigned to Böhme Fettchemie, discloses compounds of the general formula

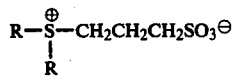

in which R is alkyl. The compounds are stated to have disinfectant and textile treating properties.

The U.K. Patent Specification No. 988,512, assigned to Tootal Broadhurst Lee Company, relates to sulfonium sulfates which are used as intermediates in the formation of certain polymers.

SUMMARY OF THE INVENTION

This invention encompasses zwitterionic surfactant compounds of the formula

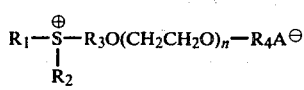

$$R_1 - \overset{\oplus}{\underset{R_2}{S}} - R_3O(CH_2CH_2O)_n - R_4A^{\ominus}$$

wherein $R_1$, $R_2$, $R_3$, $R_4$, A and n are as defined below.

DETAILED DESCRIPTION OF THE INVENTION

In its broadest aspect, the present invention relates to zwitterionic compounds comprising molecules made up of four distinct parts. Referring to the foregoing formula, the compounds herein comprise a hydrocarbon portion composed of groups $R_1$ and $R_2$; a cationic charge center which is a sulfonium ion; an anionic charge center, A; and a charge-separating moiety interposed between said cationic and anionic charge centers.

The hydrocarbon (hydrophobic) portion of the present compounds comprises straight chain, branched chain or cyclic alkyl, alkenyl, aryl, aralkyl or alkaryl moieties having from 1 to 30 carbon atoms. It will be understood by those skilled in the detergency arts that the hydrocarbon groups $R_1$ and $R_2$ can contain other substituents, such as halogen, hydroxyl, alkoxyl, and the like.

In preferred compounds according to the invention, $R_1$ and $R_2$ together contain at least 12 carbon atoms, although in certain circumstances useful compounds may be obtained when $R_1$ and $R_2$ together contain fewer than 12 carbon atoms; for example, when there is a substantial degree of hydrophobic character in the charge separating group, correspondingly less hydrophobic character is necessary on the groups $R_1$ and $R_2$ in order to obtain a compound having the requisite detersive properties. In particularly preferred compounds, group $R_1$ is a straight chain or branched chain $C_{10}-C_{30}$ alkyl moiety, or an alkaryl moiety having a $C_6-C_{26}$ alkyl group, and $R_2$ is a $C_1-C_4$ alkyl moiety or is an alkaryl or aralkyl moiety having 1 to 4 carbon atoms in the alkyl moiety, especially benzyl moiety. More preferably, $R_1$ is a $C_{12}-C_{22}$ alkyl moiety and $R_2$ is a $C_1-C_3$ alkyl moiety, especially methyl.

Other detersive surfactants are those wherein $R_1$ and $R_2$ are each independently selected from $C_6-C_{22}$ alkyl moieties and alkaryl moieties having $C_6-C_{18}$ alkyl group (preferably $R_1$ and $R_2$ are each independently selected from $C_8-C_{18}$ alkyl moieties, most preferably $C_{10}-C_{14}$ alkyl moieties).

The anionic charge center, A, is any water-solubilizing anionic moiety, and can be, for example, sulfonate, sulfate, carboxylate and the like negatively charged moieties well recognized in the detergency art as useful for imparting water-solubility to detersive surfactants. Compounds of the present type wherein A is sulfate or sulfonate, especially the former, are preferred from the standpoint of ease of manufacture and detergency performance.

The charge-separating moiety of the compounds of the present invention includes as an essential feature a polyethylene oxide chain made up of at least two ethylene oxide units. This part of the charge separating moiety is essential for the instant compounds to exhibit the good detergent properties, especially good particulate soil removal. In preferred compounds, the charge separating moiety consists in its entirety of ethylene oxide units, in which case both of the $R_3$ and $R_4$ are ethylene.

However, in its broadest aspect, the invention encompasses compounds wherein $R_3$ is a $C_2-C_8$ alkylene, alkenylene, arylene or alkarylene moiety and $R_4$ is a $C_1-C_8$ alkylene, alkenylene, arylene or alkarylene moiety. Where the anionic center, A, is a carboxylate anion, it is preferred that $R_4$ is methylene or $C_3-C_8$ alkylene, as a propionate moiety at the anionic center is relatively unstable. It will be understood that $R_3$ and $R_4$ may contain other substituents, e.g., hydroxyl, halogen, alkoxyl, and the like.

Also, in certain cases it may be desirable that $R_3$ has more than two carbon atoms. This is because the presence of a relatively labile ether oxygen atom in close proximity to the sulfur atom tends to make the compound somewhat unstable during preparation. The preparation of the compounds of the present invention can therefore be simplified if $R_3$ is, for example, a $C_3$ or $C_4$ alkylene or an arylene moiety.

In the above general formula, the number of ethylene oxide units, n, in the charge separating moiety may range from 1 to 100. The lower limit is a function of solubility, and it has been found that some compounds where n is 1 or 2 are insufficiently soluble to perform adequately as the sole surfactant in an aqueous solution. However, in combination with other surfactants, notably nonionic surfactants, the compounds of the present invention where n=1 or 2 are useful. For good clay soil removal performance, it is also important that the chain length of the charge separating moiety is not more than about 100 ethylene oxide units. To secure truly superior clay soil removal from fabrics, the degree of ethoxylation, n, is preferably from 4 to about 50, most preferably about 4 to about 20.

It will be understood that the numbers recited herein for ethylene oxide content may refer either to single compounds having, for example, 9 units of ethylene oxide per molecule, or to compound mixtures in which the average degree of ethoxylation is equal to, for example, 9 units of ethylene oxide per molecule. Commercial processes for preparing polyethylene oxide chains normally result in mixtures of compounds having a distribution of polyethylene oxide chain lengths.

As can be seen from the foregoing, the random selection of groups $R_1$ and $R_2$ for substitution at the sulphur atom and the charge separating moiety does not suffice to define detersive surfactants, rather the total hydrophobic effect resulting from the interrelation of groups $R_1$ and $R_2$ on the one hand and of $R_3$ and the ethylene oxide moiety on the other hand must be considered. In general, it can be stated that when there is a higher degree of hydrophobic character within the charge separating moiety, for example, when $R_3$ has from 4 to 8 carbon atoms, useful compounds can be obtained with $R_1$ and $R_2$ groups having less hydrophobic character.

The range of selection of group $R_4$ is somewhat less critical than the other R groups, and is usually dictated merely on the basis of the scheme used to prepare the compounds of choice. Of course, if $R_4$ is too long, water solubility of the compounds can be adversely affected. Conveniently, $R_4$ can be a $C_1-C_4$ alkylene, a $C_3-C_4$ hydroxy-substituted alkylene or a phenylene group. Most preferably, $R_4$ is ethylene except that, as noted above, when the group A is $COO^-$, $R_4$ is most preferably methylene.

The compounds of the type described hereinabove are water-soluble, (i.e., solubility of about 60 to 75 ppm, or much greater, in 105° F. water). Surprisingly, the compounds are so superior in detergency performance that only minimal solubility is required. Indeed, a solution concentration of only about 75 ppm of the present zwitterionics is sufficient to launder fabrics, although higher concentrations can be utilized to speed the cleansing process.

The synthesis of these compounds can be carried out according to the following scheme.

A polyethylene glycol having up to 100 ethylene oxide units is reacted in pyridine with an equimolar amount of p-toluenesulfonyl (tosyl) chloride to give the monotosylate compound

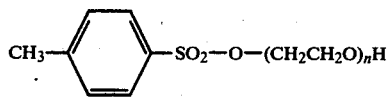   (I)

together with some of the corresponding ditosylate.

The mono-tosylate (I) is purified by chromatography and added slowly to a heated mixture of an alkyl mercaptan

   (II)

and sodium hydride in 1,2-dimethoxyethane. Refluxing of the reaction mixture for about 16 hours followed by filtering and evaporating solvent yields the thioether

   (III)

The thioether (III) can also be prepared by the more attractive commercial route in which the mercaptan (II) is ethoxylated directly with ethylene oxide in an autoclave at 140°–160° C., 540 lb. pressure and, preferably, in the presence of a base.

The thioether (III) is then sulfated using chlorosulfonic acid or sulfur trioxide, followed by neutralization to give the anionic compound

   (IV)

Finally, the compound IV is alkylated using an alkylating agent such as methyl iodide or dimethyl sulfate to give the sulfonium sulfate

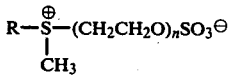   (V)

It will be understood that derivatives other than the methylated compound can be obtained by using other alkylating agents. For example, the compound (IV) can be reacted with benzyl chloride to give the analogous benzyl compound or with ethyl chloroacetate to give the carboethoxymethyl compound.

As will be discussed hereinafter, the compounds of the present invention, especially those having ethoxylate chain lengths of at least 4, and preferably 6–12 ethylene oxide units, provide useful clay soil removal performance on their own, without the need for builders or surfactants.

However, it is frequently desirable to employ the compounds of the present invention in compositions which include co-surfactants, or builders or both. In particular, compounds of the present invention having short ($n \leq 4$) ethylene oxide chains are preferably combined with a co-surfactant or builder which helps to solubilize the zwitterionic sulfonium compound.

The present invention therefore also provides detergent compositions comprising from 1% to 99% by weight of the sulfonium zwitterionic compound and from 99% to 1% of an organic detergent. The ratio of sulfonium compound the co-surfactant can be varied depending on the end use of the composition and its desired physical form. The ratio of zwitterionic compound:co-surfactant is preferably from 10:1 to 1:10, most preferably from 4:1 to 1:10 by weight. Preferred compositions comprise from 10% to 80% of zwitterionic compound and from 90% to 20% of co-surfactant.

A wide range of organic detergents can be mixed, i.e. can be considered compatible with the ethoxylated zwitterionic compounds to form compositions useful in the present invention. In the context of this invention "compatible" is defined as causing no appreciable decrease in the ability of the ethoxylated zwitterionic compound to remove and suspend particulate soil.

Classes of compatible detergents that are especially useful co-surfactants include the nonionic, zwitterionic, and ampholytic surfactants and fatty acid salts which can be used in a broad range of proportions to the ethoxylated zwitterionic compound. These co-surfactants tend to increase the clay removal performance of the sulfonium compounds, especially those with short ethoxylate chains. In contrast, most synthetic anionic detergents do not enhance the particulate soil removal performance of the ethoxylated zwitterionic compounds to the same extent, especially on synthetic fibers, although anionic surfactants can usefully be employed in combination with the sulfonium compounds for other reasons, e.g. to obtain particularly desirable sudsing characteristics. Amongst the cationic surfactants, only those having a polyoxyalkylene function are compatible with the ethoxylated zwitterionic compounds useful in the present invention.

NONIONIC SYNTHETIC DETERGENTS

Most commonly, nonionic surfactants are compounds produced by the condensation of an alkylene oxide (hydrophilic in nature) with an organic hydrophobic compound which is usually aliphatic or alkyl aromatic in nature. The length of the hydrophilic or polyoxyalkylene moiety which is condensed with any particular hydrophobic compound can be readily adjusted to yield a water-soluble compound having the desired degree of balance between hydrophilic and hydrophobic elements. Another variety of nonionic surfactant is the semi-polar nonionic typified by the amine oxide, phosphine oxides, and sulfoxides.

Examples of suitable nonionic surfactants are disclosed in Nirschl et al U.S. Pat. No. 3,862,058, Column 9, line 38 through Column 11, line 51 inclusive, which disclosures are hereby specifically incorporated by reference.

Preferred nonionic surfactants are the condensation products of primary and secondary aliphatic alcohols with ethylene oxide, including but not being limited to the Tergitol ® secondary alcohol ethoxylates manufactured by Union Carbide Corporation and the Neodol ® primary alcohol ethoxylates marketed by Shell Chemical Company. A highly preferred nonionic surfactant is Neodol 45-7, a predominantly $C_{14}$–$C_{15}$ primary OXO alcohol condensed with seven moles of ethylene oxide.

AMPHOLYTIC SYNTHETIC DETERGENTS

Ampholytic synthetic detergents can be broadly described as derivatives of aliphatic or aliphatic derivatives of heterocyclic secondary and tertiary amines in which the aliphatic radical may be straight chain or branched and wherein one of the aliphatic substituents contains from about 8 to 18 carbon atoms and at least one contains an anionic water-solubilizing group, e.g., carboxy, sulfonate, sulfato. Examples of compounds falling within this definition are sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyldodecylamino)propane-1-sulfonate, disodium octadecyl-iminodiacetate, sodium 1-carboxymethyl-2-undecylimidazole, and sodium N,N-bis(2-hydroxyethyl)-2-sulfato-3-dodecoxypropylamine. Sodium 3-(dodecylamino)propane-1-sulfonate is preferred.

ZWITTERIONIC SYNTHETIC DETERGENTS

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. The cationic atom in the quaternary compound can be part of a heterocyclic ring. In all of these compounds there is at least one aliphatic group, straight chain or branched, containing from about 3 to 18 carbon atoms and at least one aliphatic substituent containing an anionic water-solubilizing group, e.g. carboxy, sulfonate, sulfate, phosphate, or phosphonate. Examples of various classes of zwitterionic surfactants operable herein are disclosed in Nirschl et al U.S. Pat. No. 3,862,058 to Column 12, line 5 through Column 14, line 60 inclusive, which disclosures are specifically incorporated herein by reference.

Of all the above-described types of zwitterionic surfactants, preferred compounds include 3(N,N-dimethyl-N-alkylammonio)-propane-1-sulfonate and 3(N,N-dimethyl-N-alkylammonio)-2-hydroxypropane-1-sulfonate wherein in both compounds the alkyl group averages 14.8 carbon atoms in length; 3(N,N-dimethyl-N-hexadecylammonio)propane-1-sulfonate; 3(N,N-dimethyl-N-hexadecylammonio)-2-hydroxypropane-1-sulfonate; 3-(N-dodecylbenzyl-N,N-dimethylammonio)-propane-1-sulfonate; 3-(N-dodecylbenzyl-N,N,dimethylammonio)-2-hydroxypropane-1-sulfonate; N-dodecylbenzyl-N,N-dimethylammonio acetate; 3-(N-dodecylbenzyl-N,N-dimethylammonio)propionate; 6-(N-dodecylbenzyl-N,N-dimethylammonio)hexanoate; and N,N-dimethyl-N-hexadecylammonio acetate.

ANIONIC DETERGENTS

The anionic component of the instant detergent compositions can be an organic sulfuric reaction product having in its molecular structure an alkyl group containing from about 8 to about 22 carbon atoms and a sulfonic acid or sulfuric acid ester group, or mixtures thereof. (Included in the term "alkyl" is the alkyl portion of acyl groups.) Examples of this group of synthetic detersive surfactants which can be used in the present invention are the alkyl sulfates, especially those obtained by sulfating the higher alcohols ($C_8$–$C_{18}$ carbon atoms) produced from the glycerides of tallow or coconut oil; and alkyl benzene sulfonates, in which the alkyl group contains from about 9 to about 14 carbon atoms, in straight chain or branched chain configuration, e.g., those of the type described in U.S. Pat. Nos. 2,220,099 and 2,477,383, incorporated herein by reference. Linear straight chain alkyl benzene sulfonates in which the average of the alkyl groups is about 13 carbon atoms, abbreviated as $C_{13}$LAS, as well as mixed $C_{11.2}$ and $C_{11.8}$ (avg.) LAS are typically used. $C_{11}$–$C_{14}$ branched chain alkyl benzene sulfonates (ABS), which are excellent sudsers, can also be used.

Examples of commercially available alkyl benzene sulfonates (free acid form) useful in the instant invention include Conoca SA 515, SA 597, and SA 697, all marketed by the Continental Oil Company, and Calsoft LAS 99, marketed by the Pilot Chemical Company.

Other anionic surfactant compounds herein include the alkyl glyceryl ether sulfonates, especially those ethers of higher alcohols derived from tallow and coconut oil; coconut oil fatty acid monoglyceride sulfonates and sulfates; and alkyl phenol ethylene oxide ether sulfates containing about 1 to about 10 units of ethylene oxide per molecule and wherein the alkyl groups contain about 8 to about 12 carbon atoms.

Other useful anionic surfactants herein include the esters of α-sulfonated fatty acids containing from about 6 to 20 carbon atoms in the ester group; 2-acyloxyalkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Anionic surfactants based on the higher fatty acids, i.e., "soaps" are useful anionic surfactants herein. Alkali metal salts of higher fatty acids containing from about 8 to about 24 carbon atoms and preferably from about 10 to about 20 carbon atoms are useful anionic surfactants in the present compositions. Particularly useful are the soaps derivable from the mixtures of fatty acids made from coconut oil and tallow.

Preferred water-soluble anionic organic surfactants herein include linear alkyl benzene sulfonates containing from about 10 to about 18 carbon atoms in the alkyl group; branched alkyl benzene sulfonates containing from about 10 to about 18 carbon atoms in the alkyl group; the tallow range alkyl sulfates; the coconut range alkyl glyceryl sulfonates; alkyl ether (ethoxylated) sulfates wherein the alkyl moiety contains from about 12 to 18 carbon atoms and wherein the average degree of ethoxylation varies between 1 and 12, especially 3 to 9; the sulfated condensation products of tallow alcohol with from about 3 to 12, especially 6 to 9, moles of ethylene oxide; olefin sulfonates containing from about 14 to 16 carbon atoms; and soaps, as hereinabove defined.

Specific preferred anionics for use herein include: the linear $C_{10}$–$C_{14}$ alkyl benzene sulfonates (LAS); the branched $C_{10}$ to $C_{14}$ alkyl benzene sulfonates (ABS); the tallow alkyl sulfates; the coconut alkyl glyceryl ether sulfonates; the sulfated condensation products of mixed $C_{10}$–$C_{18}$ tallow alcohols with from about 1 to about 14 moles of ethylene oxide; and tallow soap.

It is to be recognized that any of the foregoing anionic surfactants can be used separately herein or as mixtures. Moreover, commercial grades of the surfactants can contain non-interfering components which are processing by-products. For example, commercial $C_{10}$–$C_{14}$ alkaryl sulfonates can comprise alkyl benzene sulfonates, alkyl toluene sulfonates, alkyl naphthalene sulfonates and alkyl poly-benzenoid sulfonates. Such materials and mixtures thereof are fully contemplated for use herein.

CATIONIC DETERGENTS

Only those cationic detergents having a hydrophilic grouping with the molecule have been found to be compatible in solution with the ethoxylated zwitterionic compounds useful in the present invention.

Thus compounds of the class

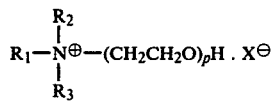

can be employed where $R_1$ is a $C_{12}$-$C_{18}$ linear or branched alkyl or alkenyl group $R_2$ and $R_3$ are $C_1$-$C_4$ alkyl or hydroxy alkyl groups, p has a value in the range 3-50, and $X^-$ is a compatible anion. Analogous bis-ethoxylated quaternary ammonium salts can also be used.

DETERGENT BUILDERS

The novel compounds of the present invention are also especially useful when combined with builders, and the invention thereof also provides detergent compositions comprising from 1% to 99% by weight of the sulfonium zwitterionic compound and from 99% to 1% of a detergent builder. The actual level of builder depends on the end use of the composition and its desired physical form; preferably, the compositions contain 10% to 75%, most preferably 25% to 60% of builder.

Suitable inorganic builders include the alkali metal polyphosphates (including the pyrophosphates and glassy high polymeric phosphates) phosphonates, carbonates, sesquicarbonates, bicarbonates, borates, silicates, sulphates, and aluminosilicates.

Aluminosilicate builder salts found to be useful in the present invention have the general formula:

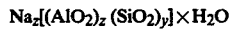

wherein z and y are integers of at least 6, the molar ratio of z to y is in the range from 1.0 to about 0.5 and x is an integer from about 15 to about 264. Such alumino-silicates also should have a particle size diameter in the range 0.1 to 100 microns, a calcium ion exchange capacity of at least about 200 milligram $CaCO_3$ equivalent/gram and a calcium ion exchange rate of at least about 2 grains/U.S. gallon/minute/gram. Detergent compositions incorporating alumino-silicate builder salts of this type are disclosed in the commonly assigned Belgian Pat. No. 814,874 issued Nov. 12, 1974 which disclosure is incorporated herein by reference.

Suitable water soluble detergent builders are disclosed in Nirschl U.S. Pat. No. 3,862,058 at column 15, line 8 to column 16, line 18 which disclosures are incorporated herein by reference. Examples of organic builders are set forth in Diehl U.S. Pat. No. 3,308,067 and mixtures of certain preferred organic and inorganic builders are disclosed in Canadian Pat. No. 755,038, the disclosures of both patents being hereby incorporated by reference.

The above-discussed builders can also usefully be incorporated into the detergent compositions comprising a mixture of the sulfonium/zwitterionic compound and a co-surfactant.

OPTIONAL INGREDIENTS

In addition to the above-mentioned compounds, detergent compositions according to the invention may also contain other ingredients conventionally employed in such products.

One such optional ingredient that may be incorporated is an enzyme for removal of protein-based or carbohydrate-based stains. Enzymes for removing protein-based stains are proteolytic in nature such as those sold under the trade names "Alcalase" and "Esterase" by Novo Industries A/S Denmark or under the trade names "Maxatase" and "AZ Protease" by Gist-Brocades N.V. The Netherlands. These materials are normally incorporated at levels of up to 1% by weight, preferably 0.25% to 0.75% by weight, and are preferably coated or prilled with inert additives to minimize dust formation and improve storage stability. A wide range of enzyme materials and means for their incorporation into synthetic detergent granules is disclosed in U.S. Pat. No. 3,553,139 issued on Jan. 5, 1971, to McCarty, Roald, DeOude, Blomeyer, and Cracco which disclosure is hereby incorporated by reference.

A further ingredient that may be incorporated to improve product performance is a bleaching agent of the halogen or oxygen-containing type. Examples of the hypohalite bleach type include trichloro isocyanuric acid and the sodium and potassium dichloroisocyanurates and N-chloro and N-bromo alkane sulphonamides. Such materials are normally added at 0.5%-10% by weight of the finished product, preferably 1%-5% by weight.

Examples of oxygen-containing bleaches include sodium perborate, sodium percarbonate, and potassium non-opersulphate that are incorporated at levels of 5-30%, preferably 10-25% by weight of the final product. The inclusion of organic bleach activators such as phthalic anhydride, tetra acetyl ethylene diamine, tetra acetyl methylene diamine or tetra acetyl glycouril lead to the in situ production during the washing process of the corresponding organic peroxy acids which have enhanced low temperature bleaching performance. Activators of this type are normally used with sodium perborate, at usage levels of 5-15% by weight of the final product.

Materials to boost or modify the sudsing pattern of the compositions of the present invention may also be included. Examples of suds boosters include coconut and tallow mono- and di-alkanolamides, particularly ethanolamides and $C_{12-15}$ alkyl di-lower alkyl amine oxides. Typical suds depressors include long chain fatty acids such as those disclosed in U.S. Pat. No. 2,954,347 issued Sept. 27, 1960, to Wayne St. John and combinations of certain nonionics therewith as disclosed in U.S. Pat. No. 2,954,348 issued Sept. 27, 1960, to Eugene Schwoeppe, both disclosures being incorporated herein by reference.

Other optional ingredients in granular products include hydrotropes and anticaking additives such as salts of lower alkyaryl sulphonic acids, salts of $\alpha$-sulphobenzoic acid, and urea, normally utilized at levels of 0.5% to 5% by weight of the final product, preferably at levels of 1%-3% by weight. $C_{12}$-$C_{18}$ alkyl acid phosphates and their condensation products with ethylene oxide may also be incorporated at similar levels for control of crutcher mix viscosity. Antiredeposition agents such as glassy polymeric phosphates, magnesium silicates, colloidal silicas, carboxymethyl cellulose, hydroxyethyl cellulose, and their derivatives may also be incorporated. Preferred anti-redeposition agents are glassy phosphates containing more than ten phosphorus atoms per molecule and colloidal silicas.

Anti-tarnish and anti-corrosion agents, perfume and color may also be included, the last ingredient being conveniently added either as a general color or in the form of a speckle applied to a separate granule fraction of the entire formulation or to a granulate of one or more of the ingredients.

Anionic optical brightening agents or fluorescers such as the bis(triazinylamino)stilbene disulphonates can be included in the formulations of the present invention but their efficiency is not as high as in conventional formulations unless they are incorporated together with an anionic surfactant.

The pH of detergent formulations in accordance with the present invention can lie anywhere within the range 4-11 but is preferably chosen to fall within the range 6-10. However, the use of specific optional components such as enzymes may require the selection of a product pH that will permit optimum functioning of the component concerned.

Granular formulations embodying the compositions of the present invention may be formed by simple admixture of the components, by adsorption of the surfactant onto a carrier granule, by an atomizing and spray-drying process, or by pan or drum granulation of the components.

Liquid or pasty formulations embodying the compositions of the present invention may contain builders or may be unbuilt. If the compositions are unbuilt, they contain from 10%-90% of total surfactant in aqueous or alcoholic solution. Optionally, such liquid compositions can include from 1%-10% of an organic base such as mono, di, or tri-alkanolamine. Such compositions will normally be homogeneous single phase liquids of low viscosity (approximately 100-150 centipoises at 75° F.).

Built liquid detergent compositions may also be single phase liquids provided that the builder can be solubilized in the mixture at its level of use. Such liquids may contain 5%-30% total surfactant, 10%-20% builder which may be organic or inorganic, 5%-10% of a hydrotrope system and 40%-80% of water. Liquids of this type also have low viscosity (100-150 c.p.s. at 75° F.).

Built liquid detergents incorporating components that form heterogeneous mixtures or levels of builder that cannot be completely dissolved can also embody the compositions of the present invention. Such liquids conventionally employ viscosity modifiers to produce systems having plastic shear characteristics to maintain stable dispersions and to prevent phase separation or solid settlement.

PERFORMANCE DATA

In this specification the assessment of particulate soil removal performance both of detergent formulations of the invention and of comparative formulations is carried out using the following procedure.

Soil removal testing is carried out in a washing machine simulator and involves a 10-minute wash cycle at 105° F. in 7 grans per U.S. gallon hard water (calculated as $CaCO_3$) using a 3:1 ratio of Ca:Mg salts. The fabrics are washed, rinsed and tumble-dried prior to being graded on a Gardner whiteness meter. The fabric load for particulate soil removal testing comprises a mixture of white cotton, polycotton (65% DACRON®/35% cotton), and polyester (KODEL®) swatches which are stained with a standardized clay-type soil.

The results (expressed as relative clay removal index) for each formulation represent a percentage of the whiteness value achieved by a commercial synthetic detergent standard tested at the same time under identical conditions. This standard formulation has the following composition by weight:

| | |
|---|---|
| Sodium $C_{12}$ alkylbenzene sulphonate | 7.55 |
| Sodium tallow alkyl sulphate | 9.25 |
| Coconut alcohol + 6 mole EO | 0.60 |
| Diethanolamide | 1.60 |
| Sodium tripolyphosphate | 50.00 |
| Sodium silicate solids | 5.90 |
| Sodium sulphate | 14.20 |
| Moisture | 10.00 |
| Miscellaneous | 0.30 |
| | 100.00 |

Performance data was obtained using three representative compounds of the present invention. These three compounds had the general formula

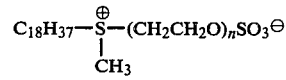

where n is, respectively, 3, 9 and average 17. These three compounds are below designated $E_3$, $E_9$ and $E_{17}$ respectively.

Table 1 shows the clay soil removal performance of the zwitterionic compounds themselves in water.

TABLE 1

| COMPOUND | LEVEL IN SOLUTION (ppm) | CLAY REMOVAL INDEX | | |
|---|---|---|---|---|
| | | COTTON | POLY-COTTON | POLYESTER |
| $E_3$ | 250 | 29 | 40 | 27 |
| $E_9$ | 250 | 101 | 98 | 108 |
| $E_{17}$ | 250 | 107 | 98 | 101 |
| $E_9$ at pH 10.5 | 250 | 88 | 99 | 97 |

The table shows that the clay removal performance of $E_3$ on its own is poor; this is attributable to the incomplete solubility of this compound. The completely soluble $E_9$ and $E_{17}$ compounds have a performance equal to that of the control composition, even in the absence of co-surfactants or builders.

As can be seen from the data obtained for $E_9$ at pH 10.5, there was no substantial decrease in performance indicating that the zwitterionic compound is stable at this pH.

Table 2 shows the clay removal performance of compositions including a builder.

TABLE 2

| SURFACTANT | SURFACTANT LEVEL | BUILDER | BUILDER LEVEL | CLAY REMOVAL COTTON | POLY-COTTON | POLYESTER |
| --- | --- | --- | --- | --- | --- | --- |
| $E_3$ | 250 | Sodium carbonate<br>Sodium silicate<br>(3.2:1 ratio $SiO_2:NaO_2$) | 200<br>200 | 46 | 50 | 39 |
| $E_9$ | 250 | Sodium Tripolyphosphate | 250 | 112 | 107 | 102 |

It can be seen that builders significantly improve the performance of the poorly-soluble $E_3$ compound and also offer some advantage in combination with the $E_9$ compound.

Table 3 shows the effect of combining various co-surfactants with the sulfonium compounds.

TABLE 3

| ZWITTERIONIC COMPOUNDS | COMPOUND LEVEL ppm | CO-SURFACTANT | CO-SURFACTANT LEVEL ppm | CLAY REMOVAL INDEX COTTON | POLY-COTTON | POLY-ESTER |
| --- | --- | --- | --- | --- | --- | --- |
| $E_3$ | 125 | *Neodol 45-7 | 125 | 52 | 82 | 68 |
| $E_3$ | 125 | $C_{12}$ Alkyl Benzene Sulfonate | 125 | 26 | 44 | 33 |
| $E_{17}$ | 125 | $C_{18}H_{37}S(CH_2CH_2O)_{17}SO_3^\oplus Na^\oplus$ | 125 | 86 | 84 | 63 |
| $E_{17}$ | 125 | Neodol 45-7 | 125 | 102 | 95 | 99 |
| $E_{17}$ | 125 | $RO(CH_2CH_2O)_{2.25}SO_3^\ominus Na^\oplus$ where R is $C_{14}$-$C_{16}$ alkyl | 125 | 88 | 76 | 66 |
| $E_{17}$ | 125 | Na Stearate | 125 | 101 | 91 | 100 |

*Neodol 45-7 is a linear primary $C_{14-15}$ condensed with an average of 7 moles of ethylene oxide per mole of alcohol, marketed by Shell Chemical Co.

As can be seen from the above table, various co-surfactants can be combined with the sulfonium compounds to give useful compositions. The performance of the poorly soluble $E_3$ compound is markedly improved by the addition of a nonionic surfactant (Neodol 45-7), the nonionic surfactant serving to solubilize the zwitterionic as well as providing a synergistic effect.

Table 4 shows performance data for compositions formulated both with co-surfactant and builder.

perature. No decrease in clay soil removal performance of the compositions was observed at the end of this time.

Additional examples of formulations which show satisfactory performance even after prolonged storage are as follows:

| Liquid Product | |
| --- | --- |
| $C_{18}H_{37}S^\oplus(CH_2CH_2O)_{17}SO_3^\ominus$<br>\|<br>$CH_3$ | 25.0% |
| Triethanol amine | 10.0% |
| HCl | 1.2% |
| Water | 63.8% |

TABLE 4

| ZWITTERIONIC COMPOUND AND LEVEL (ppm) | CO-SURFACTANT AND LEVEL (ppm) | BUILDER AND LEVEL (ppm) | CLAY REMOVAL INDEX COTTON | POLY-COTTON | POLYESTER |
| --- | --- | --- | --- | --- | --- |
| $E_{17}$; 125 | Na Stearate; 125 | STP, 250 | 108 | 101 | 104 |
| $E_{17}$; 125 | $C_{18}H_{37}S(CH_2CH_2O)_{17}SO_3^\ominus Na^\oplus$ 71 | STP, 250 | 90 | 83 | 68 |
| $E_{17}$; 125 | $PO(CH_2CH_2O)_{2.25}SO_3^\ominus Na^\oplus$ where R is $C_{14-16}$ alkyl; 125 | STP, 250 | 93 | 79 | 79 |
| $E_{17}$; 125 | Neodol 45-7; 125 | STP, 250 | 101 | 99 | 101 |

The above compositions offer good clay soil removal performance at a builder level which is very low when compared with many conventional, heavy-duty detergent products.

In order to obtain a measure of the stability of the zwitterionic compounds of the present invention, compositions comprising $$C_{18}H_{37}S^\oplus(CH_2CH_2O)_3SO_3^\ominus \text{ and}$$
$$|$$
$$CH_3$$

$$C_{18}H_{37}S^\oplus(CH_2CH_2O)_9SO_3^\ominus$$
$$|$$
$$CH_3$$

were allowed to stand for about 2½ weeks in a carbonate/silicate slurry at about pH 10.5 and room tem-

| Powder Admix | |
| --- | --- |
| $C_{18}H_{37}S^\oplus(CH_2CH_2O)_{17}SO_3^\ominus$<br>\|<br>$CH_3$ | 38.4% |
| Sodium carbonate | 30.8% |
| Sodium silicate ($SiO_2:Na_2O=3.2$) | 30.8% |

The following examples serve to illustrate the invention.

EXAMPLE I

Preparation of 8-methyloctadecylsulfonio-3,6-dioxaoctyl sulfate (A) Preparation of 8-iodo-3,6-dioxaoctanol One hundred grams (0.59 mole) of 2-[2-(2-chloroethoxy)ethoxy]-ethanol (Aldrich 16,297-3) was added to a solution of 450 g. (3 mol) of sodium iodide in 2.5 l acetone and stirred, in the dark, for 5 hours at reflux and then at room temperature for 16 hours. The precipitate was filtered and the acetone evaporated off at 30° C. The residue was dissolved in chloroform, extracted with saturated sodium chloride solution, and then with saturated sodium bisulfate solution. The chloroform extract was dried (MgSO4) and evaporated at room temperature to yield 137 g. (53%) of the title compound.

(B) Preparation of 3,6-dioxa-9-thiaheptacosanol

To a solution of 31.5 g. (0.11 moles) of n-octadecanethiol in 200 ml. of 1,2-dimethoxyethane which had been heated to 40° C., under argon, was added slowly 0.11 moles of sodium hydride (5.3 g. 50%) which had been rinsed with hexane to remove the mineral oil and then slurried in 1,2-dimethoxyethane. The reaction mixture was then heated at reflux (85° C.) with stirring for 2 hours. A solution of 39 g. (0.11 mole) of the monoiodide in 200 ml of 1,2-dimethoxyethane was added dropwise, and the reaction mixture was allowed to reflux with stirring for 16 hours. The mixture was cooled, the insoluble salts filtered, and the solvent evaporated. The residue, a mixture of the title compound and sodium iodide, was dissolved in chloroform and washed with water. The chloroform extract was dried, evaporated, and the residue crystallized from hexane to yield 11.5 g. (0.027 26% yield) of the title compound.

(C) Preparation of sodium 3,6-dioxa-9-thiaheptacosyl sulfate 3,6-Dioxa-9-thiaheptacosanol, (11.5 g, 0.027 mole) was sulfated with chlorosulfonic acid (0.14 mole) by the general sulfation procedure described below to afford the title compound.

(D) Preparation of 8-methyloctadecylsulfonio-3,6-dioxaoctyl sulfate

The sodium 2,6-dioxa-9-thiaheptacosyl sulfate was dissolved in methanol and 92 g (0.65 mole) of methyl iodide was added. The reaction mixture was refluxed with stirring for 6 hours. Insoluble salts were filtered and the methanol and excess methyl iodide were evaporated. The residue was purified by the mixed-bed ion-exchange method described below and crystallized from ether to yield 4.0 g. (0.008 mole) of a white powder which was identified as the compound

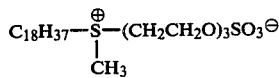

EXAMPLE II

Preparation of 26-methyloctadecylsulfonio-3,6,9,12,15,18,21,24-octaoxahexacosyl sulfate (A) Preparation of Nonaethyleneglycol Under nitrogen, 46 grams (2 moles) of sodium pellets were added cautiously to 2,664 ml (20 moles) of previously dried and distilled triethyleneglycol. The temperature was kept below 100° C. After all the sodium had reacted, the temperature was adjusted to 100° C. and 187 grams (1 mole) of 1,2-bis-(2-chloroethoxy) ethane was added in a slow stream. The mixture was heated overnight at 100° C. (still under nitrogen) and then filtered hot to remove most of the sodium chloride. Excess triethyleneglycol was stripped under vacuum and the mixture was again filtered while hot. The material was purified by molecular distillation and has a b.p. of 170°–175° C. at 0.001 mm.

(B) Preparation of 26-hydroxy-3,6,9,12,15,18,21,24-octaoxahexacosyl p-toluenesulfonate One hundred grams (0.24 moles) of nonaoxyethylene glycol was dissolved in 300 ml dry pyridine and cooled to 0° C. An equal molar amount of tosyl chloride was added in small portions with stirring. The reaction mixture was then stirred at 0°–5° C. for 5 hours, poured into an equal volume of cold water and acidified to pH 3 with 6N hydrochloric acid. The solution was extracted 3 times with chloroform, dried (MgSO4), and evaporated. The residue, 124 g., was a pale yellow liquid, slightly viscous. TLC (silica gel GF, I2, 95% butanone-5% H2O) indicated a mixture of unreacted glycol ($R_f$ 0.1), the monotosylate ($R_f$ 0.5) and the ditosylate ($R_f$ 0.9). One hundred grams of the reaction mixture was dissolved in a minimal amount of 2-butanone and passed through 1000 g. of silica gel 100–200 mesh MCB SX144-06 grade 923. The column was eluted with 2-butanone; 41 g. of pure monotosylate was isolated. The product was a colorless oil which was characterized by I.R. (two sharp bands at 1180 and 1190 cm$^{-1}$) and proton NMR.

(C) Preparation of 3,6,9,12,15,18,21,24-octaoxa-27-thiapentatetracontanol

To a heated (40° C.) solution of 20.1 g (0.97 mole) of n-octadecanethiol in 200 ml of dried 1.2-dimethoxyethane was slowly added under argon 0.07 mole (3.4 g., 50%) of sodium hydride (rinsed with hexane to remove the mineral oil) slurried in 1,2-dimethoxyethane. The reaction mixture was then heated at reflux (85° C.) with stirring for 2 hrs. A solution of 40 g. (0.07 mole) of the nonaethylene glycol monotosylate in 200 ml. 1,2-dimethoxyethane was added dropwise and the reaction mixture allowed to reflux with stirring for 16 hours. The mixture was cooled, insoluble salts were filtered, and the solvent was evaporated to yield a near quantitative yield (0.07 mole) of the thioether.

(D) Preparation of sodium 3,6,9,12,15,18,21,24-octaoxa-27-thiapentatetracontyl sulfate 3,6,9,12,15,18,21,24-Octaoxa-27-thiapentatetracontanol (49 g., 0.07 mole) was sulfated according to the general procedure described below using 88 g. (0.76 mole) of chlorosulfonic acid to yield the title compound.

(E) Preparation of 26-Methyloctadecylsulfonio 3,6,9,12,15,18,21,24-octaoxahexacosyl sulfate Sodium 3,6,9,12,15,18,21,24-octaoxa-27-thiapentatetracontyl sulfate was dissolved in 300 ml MeOH and 75 ml (1.2 moles) of methyl iodide was added. The mixture was heated at reflux 21 hours. The MeOH and excess methyl iodide were evaporated, the residue was purified by two mixed-bed ion-exchange treatments, and crystallized from ether which gave 4 g. (0.005 moles) of a white crystalline solid, identified as the compound

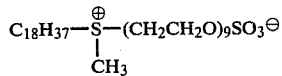

EXAMPLE III

Preparation of a polyoxyethylene (average monomer units=17) separated methyloctadecylsulfoniosulfate (A) Preparation of polyoxyethyl (n=~17) octadecyl sulfide 1-Octadecanethiol, 250 g. (0.87 mole), was dissolved in 250 ml of bis-(2-methoxyethyl) ether. Three grams (0.13 mole) of cut sodium spheres were added and the reaction mixture was transferred to a rocking autoclave and ~462 g. of ethylene oxide was bled into the autoclave over a period of 3 hours at 140°-160° C. The maximum pressure observed was 540 lbs. After all the ethylene oxide had been added, rocking was continued for an additional hour. The mixture was cooled, the bis-(2-methoxyethyl) ether was evaporated under reduced pressure, and the residue crystallized from hexane to give a white solid in 65% yield based on the octadecane thiol.

(B) Preparation of sodium polyoxyethylene (n=~17) separated octadecylthiasulfate A solution of 556 g. (0.54 mole) of the ethoxylated mercaptan dissolved in 2 liters dry pyridine was cooled to −5° to 0° C. under argon. Chlorosulfonic acid, 115 ml (117 mole), was added dropwise very slowly over a period of 7 hours, during which time the temperature was kept below 10° C. by continued cooling. The mixture was then stirred at room temperature overnight and made basic by adding 600 ml cold 25% sodium hydroxide. An additional liter of distilled water was added, the solution extracted twice with chloroform, dried (MgSO4), and concentrated to give 551 g (0.49 mole) of the crude sulfate which was then crystallized from 2 liters of acetone to give 358 g of the title compound.

(C) Preparation of polyoxyethylene (n=~17) separated methyloctadecylsulfoniosulfate To a solution of 165 g (0.15 mole) of sodium polyoxyethylene n=~17) separated octadecylthiasulfate dissolved in 2 liters of hexane was added 57 g. (0.45 mole) of freshly distilled dimethylsulfate. The mixture was stirred at reflux for 2 hours. The product was insoluble in hexane and separated from the hexane as an oil. The hexane was decanted and the residue was rinsed with hexane. The residue was purified by two mixed-bed ion exchange treatments: (1) 800 g. mixed bed resin for 16 hours, and (2) 800 g. mixed bed resin for 4½ hours. Crystallization from ether gave 76 g. of the title compound as a white powder (45% yield).

GENERAL SULFATION PROCEDURE

The alcohol was dissolved in dry pyridine (4×weight basis) and cooled to 0° C., under argon. A 3 molar excess of chlorosulfonic acid was added dropwise very slowly over a period of 3 to 7 hours, during which time the temperature was kept below 20° C. by continued cooling. The reaction mixture was then allowed to warm to room temperature and stirring was continued for an additional 2-16 hours. The mixture was then made basic by slowly pouring with stirring into a two molar excess of cold 25% NaOH. The solution was extracted 3 times with chloroform, dried (MgSO4), and evaporated.

GENERAL PURIFICATION PROCEDURE OF ZWITTERIONICS BY ION EXCHANGE

The crude zwitterionic was dissolved in methanol and stirred 6-24 hours with a 10 molar equivalent excess of mixed bed resin, which had been soaked and rinsed with methanol. The mixed bed resin used was Rohm and Haus, Amberlite monobed IRN-150, G-0425 technical grade, or Fisher R-207, Rexyn 300 H-OH. The average total exchange capacity of the wet volume resin was about 1 meq/g. After stirring, the resin was filtered by use of a Buchner funnel and vacuum aspirator and rinsed several times with methanol. The methanol was evaporated or additional distilled water was added and the solution extracted three times with chloroform. The chloroform was dried (MgSO4) and evaporated to give the pure zwitterionic.

What is claimed is:

1. A detersive compound of the formula

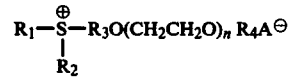

wherein $R_1$ and $R_2$ are each straight chain, branched chain or cyclic alkyl, alkenyl, aryl, aralkyl or alkaryl moieties having from 1-30 carbon atoms; $R_3$ is a $C_2$–$C_8$ alkylene; $R_4$ is a $C_1$–$C_8$ alkylene; A is a sulfate moiety; and n is from 1 to about 100.

2. A compound according to claim 1 wherein $R_1$ is a straight chain or branched chain $C_{10}$–$C_{30}$ alkyl moiety or an alkaryl moiety having a $C_6$–$C_{26}$ alkyl group and $R_2$ is a $C_1$–$C_4$ alkyl moiety or is an alkaryl or aralkyl moiety having 1 to 4 carbon atoms in the alkyl moiety.

3. A compound according to claim 2 wherein $R_1$ is a $C_{12}$–$C_{22}$ alkyl moiety; $R_2$ is a $C_1$–$C_3$ alkyl moiety, or a benzyl moiety; $R_3$ is a $C_2$–$C_4$ alkylene moiety and $R_4$ is ethylene; and n is from 4 to 50.

4. A compound according to claim 1 wherein $R_1$ is $C_{18}$ alkyl, $R_2$ is methyl, and n is from 4 to 20.

5. A compound according to claim 1 wherein $R_1$ and $R_2$ are each independently selected from $C_6$–$C_{22}$ alkyl moieties and alkaryl moieties having $C_6$–$C_{18}$ alkyl groups.

6. A compound according to claim 5 wherein $R_1$ and $R_2$ are each $C_8$–$C_{18}$ alkyl moieties.

7. A compound according to claim 5 wherein $R_3$ is a $C_2$–$C_4$ alkylene moiety and $R_4$ is ethylene and n is from 4 to 50.

* * * * *